United States Patent [19]
Blanton

[11] Patent Number: 5,688,260
[45] Date of Patent: Nov. 18, 1997

[54] REUSABLE FABRIC FEMININE HYGIENE DEVICE

[76] Inventor: Catherine Carroll Blanton, 176 Genung Rd., Ithaca, N.Y. 14850

[21] Appl. No.: 552,385

[22] Filed: Nov. 3, 1995

[51] Int. Cl.⁶ .................................................. A61F 13/20
[52] U.S. Cl. ............................................. 604/904; 604/11
[58] Field of Search ............................... 604/11–18, 904

[56] References Cited

U.S. PATENT DOCUMENTS

| | | |
|---|---|---|
| 2,487,200 | 11/1949 | Trager . |
| 2,629,381 | 2/1953 | Brown . |
| 3,058,468 | 10/1962 | Griswold et al. . |
| 3,845,767 | 11/1974 | Friese et al. . |
| 4,108,180 | 8/1978 | Moehrle . |
| 4,217,900 | 8/1980 | Weigner et al. . |

OTHER PUBLICATIONS

Glad Rags, Brochure.
Healthy Alternative, Brochure.

*Primary Examiner*—John G. Weiss
*Assistant Examiner*—Ki Yong
*Attorney, Agent, or Firm*—Jones, Tullar & Cooper, P.C.

[57] ABSTRACT

A reusable, washable, internally worn catamenial device is fabricated by folding a rectangular cloth to produce two elongated side-by-side multilayered cloth tubes. A withdrawal string is looped through both tubes. The folded cloth may be stitched to provide hems along selected edges of the cloth and to provide a central seam which forms and adjoins the tubes.

14 Claims, 2 Drawing Sheets

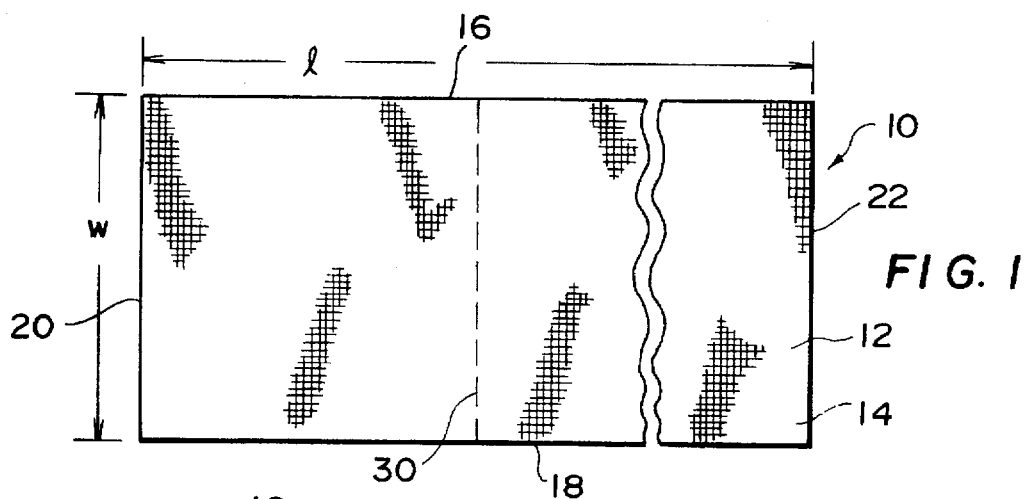
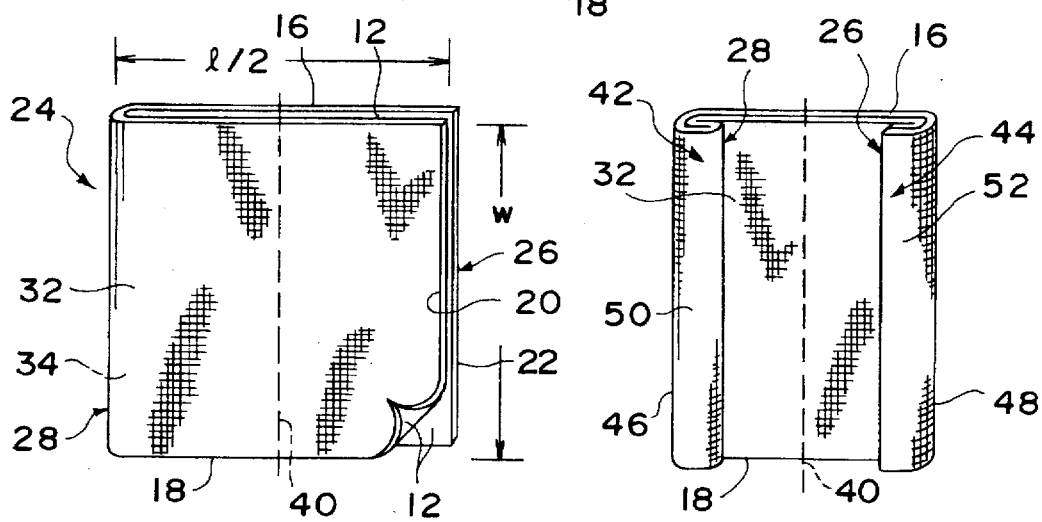
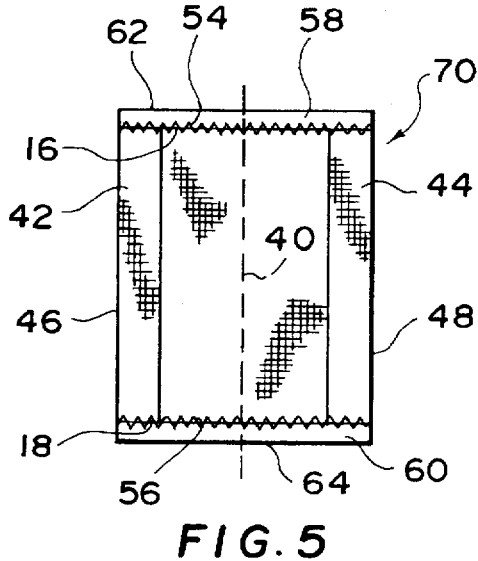
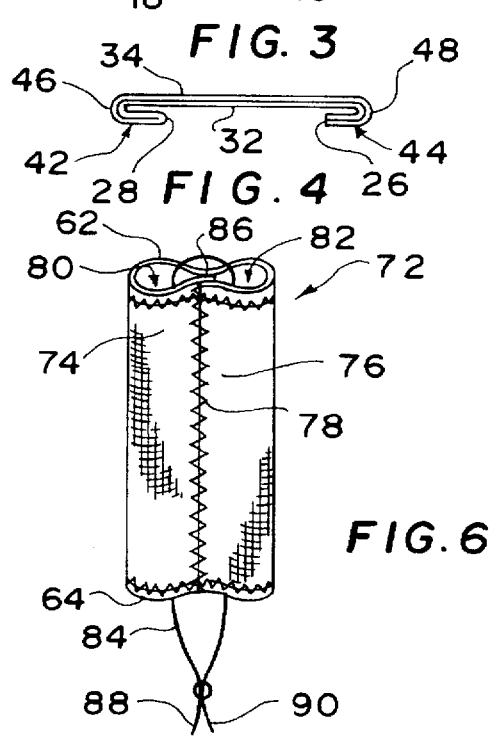

REUSABLE FABRIC FEMININE HYGIENE DEVICE

The present invention relates, in general, to feminine hygiene products, and more particularly to a washable, reusable, fabric, internally worn, device for collecting vaginal discharges.

A wide range of feminine hygiene products are available on the market, primarily in the form of internally worn tampons, externally worn pads and the like. Internally worn tampon products generally take the form of a compressed mass of fibers which is designed to absorb and retain fluids such as menstrual, with innumerable variations on this basic concept having been developed over the years in attempts to overcome various disadvantages of available products. However, problems still exist, for available products are expensive and wasteful, and do not meet the everyday needs of women.

More particularly, such internally worn products generally are in the form of a generally cylindrical, compressed mass of material which does not conform to the internal shape of the vagina, and which is therefore uncomfortable to wear and in some cases may be ineffective, or might even tend to fall out, or be ejected, during strenuous exercise or exertion. Such products typically fail to provide a variety of sizes sufficient to accommodate wide range of vaginal discharges of women of all ages or for use under varying conditions, with the result that they can produce excessive dryness of tissues which may lead to a variety of illnesses. Further, they often are made from, or include, materials which can cause allergic reactions in the wearer.

Prior tampon devices present a further problem in that they can pull apart, or shred, upon removal, leaving small remnants in the vagina which can be a magnet for bacteria. Additionally, such prior products present significant disposal problems, which make users reluctant to change them at appropriate intervals. All of these difficulties make it evident that there is a significant need for an improved feminine hygiene product.

SUMMARY OF THE INVENTION

Briefly, the present invention is directed to a reusable, washable, internally worn hygiene product which overcomes the numerous disadvantages of existing products. In accordance with the invention, such an improved product is a fabric tampon which preferably consists of a single piece of cotton cloth folded and stitched to provide two parallel, side-by-side, elongated, multilayered cloth tubes. A withdrawal cord is looped through the tubes for use in removing the tampon. The device is simple to manufacture, and is washable and immediately reusable. The cotton fabric readily conforms to the shape of the user to ensure comfort and improved absorption of menstrual fluids and effective absorption of other types of vaginal discharge. The fabric used for the product is strong and stable, so that it will not shred, but will retain its shape and absorbency through many washings and reuses.

The product can be made in a wide range of sizes, is suitable for use by women of all ages, and because of its improved fit, the tampon product of the present invention will remain in place to provide worry-free protection. The preferred cotton fabric is non-allergenic and does not produce excessive drying of tissues, so that it can be used daily. The product can be used safely for as long as it is needed.

The material is 100% biodegradable, and because it is reusable not only is the cost of purchasing the product significantly reduced, but disposal problems are substantially eliminated. Further, because fewer products must be purchased, less packaging is required, so that the product is environmentally sound.

If desired, the product may be packaged as a part of a complete personal hygiene system which may include a variety of tampon sizes, storage containers for both clean and soiled tampons, and a net bag for holding tampons during washing. The package might also contain a travel case for smaller quantities including a small storage container, and might include a purse tote for one or two tampons and reusable plastic storage envelopes.

The product of the present invention thus overcomes the problems of prior tampon devices, and provides a simple, inexpensive and comfortable tampon which is completely reusable.

DESCRIPTION OF PREFERRED EMBODIMENT

The foregoing, and additional objects, features and advantages of the present invention will become evident from a consideration of the following detailed description of a preferred embodiment thereof, taken in conjunction with the accompanying drawings in which:

FIG. 1 is a top plan view of a cotton fabric from which the tampon of the present invention is fabricated;

FIG. 2 is a top plan view of the fabric folded a first time, in a first step of a fabrication process;

FIG. 3 is a top plan view of the fabric folded a second time, in a second step of the fabrication process;

FIG. 4 is an end view of the folded fabric of FIG. 3;

FIG. 5 is a top plan view of the fabric folded a third time, and stitched in third and fourth steps of the fabrication process;

FIG. 6 is a perspective view of the fabric folded a fourth time to produce parallel tubes and with a string inserted in fifth and sixth steps of the process;

DESCRIPTION OF PREFERRED EMBODIMENT

Figure 7:
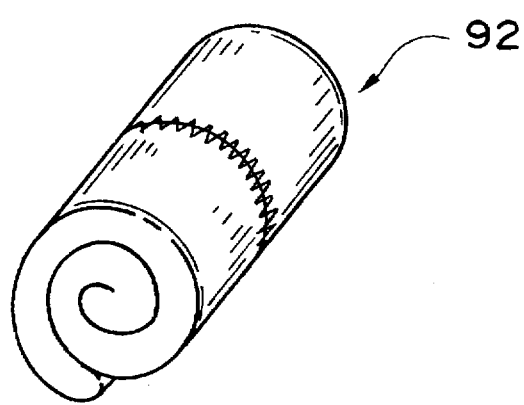
FIG. 7 is a perspective view of the tampon of FIG. 6 rolled for insertion.

Turning now to a more detailed consideration of the present invention, there is illustrated in FIG. 1 a piece of fabric such as a woven rectangular cloth 10, from which the tampon of the invention may be fabricated. The cloth has front and back surfaces 12 and 14 and a periphery defined by upper and lower edges 16 and 18 and side edges 20 and 22. The fabric preferably is a 100% cotton cloth closely, but not tightly, woven to form a moisture absorbent, soft layer of the type commonly used for diapers. The material may take a variety of shapes and sizes, but in one form, the edges 16 and 18 may have a length L of about 9 inches defining the length of the cloth, and the edges 20 and 22 may be about 4.5 inches long, defining the width W of the cloth. The thickness of the cloth will depend on the size of the thread and on the weave and may be in the range of about 0.01 to 0.05 inch, although this can vary widely.

In fabricating the tampon, the cloth 10 is first folded to one-half its original length, producing a base member 24 having a width W equal to that of cloth 10, and having a length L/2. The base member is illustrated in this embodiment as a square, although other preferably rectangular shapes may be provided, depending on the desired finished size of the tampon. The member 24 includes top and bottom edges 16 and 18, of cloth 10 which are folded in half, with the side edges 20 and 22 of the cloth 10 being brought together to form a new side edge generally indicated at 26 opposite a new side edge 28 formed at a vertical fold line 30 (FIG. 1). The resulting multilayer member 24 has front and rear surfaces 32 and 34, respectively, which are formed of the rear surface 14 of cloth 10. The front surface 12 of cloth 10 is folded inside the member 24.

The second step in fabricating the tampon is illustrated in FIG. 3, wherein the side edges 26 and 28 are folded inwardly toward each other and toward a common central, or longitudinal vertical axis 40 midway between those edges. Preferably, the two side edges 26 and 28 are folded in directions transverse to axis 40 about one-third their respective distances to the central axis 40 to form oppositely disposed side panels 42 and 44 overlying the front surface 32 of member 24. The panels 42 and 44 have folded panel outer side edges 46 and 48, respectively, which are parallel to central axis 40 and panel inner side edges 28 and 26, respectively. As illustrated, the rear surface 34 of member 24 becomes the front surfaces 50 and 52 of panels 42 and 44, respectively.

The third and fourth fabrication steps include folding the top and bottom edges 16 and 18 inwardly toward each other along the central axis 40 and stitching the edges as illustrated at 54 and 56 to form upper and lower opposed hems 58 and 60, respectively. The folded hems provide upper and lower edges 62 and 64 of a tampon blank generally indicated at 70 these edges being transverse to central axis 40.

Blank 70 is folded into its final form as a tampon 72, illustrated in FIG. 6, in a fifth fabrication step. In this step, the edges 46 and 48 of blank 70 are folded inwardly in a direction transverse to axis 40 to provide opposed flaps 74 and 76 which overlap each other and which overlap the central axis 40. The blank is then stitched along the axis 40 as indicated at 78, with the stitches 78 passing through blank edges 46 and 48 and through the two layers of the cloth 24 along axis 40. The longitudinal stitching 78 forms a seam which secures the edges 46 and 48 of flaps 74 and 76 to the cloth to form two parallel, vertical (or longitudinal) adjacent tubes 80 and 82 extending from the top edge 62 to the bottom edge 64 of the blank 70.

A thin withdrawal string or cord 84 is then passed up through one tube, such as tube 80, from the bottom edge 64 to the top edge 62 of the blank, is passed over the top end 86 of the longitudinal seam formed by stitching 78, and is passed downwardly through adjoining tube 82. Ends 88 and 90 of the string 80 are secured together, as by a knot, to hold the string in place within the tampon.

The elongated parallel tubes 80 and 82 may be made of any desired length and diameter, and with any desired number of layers of cloth material, so that a wide range of sizes and absorbency can be provided. Thus, for example, the cloth 10, although preferably a single layer, may be made up of multiple layers, and may be folded a number of times to produce the base member 24. Alternatively, base member 24 may be a thick single layer of cloth, so that the first folding step can be omitted. Although the cloth preferably is 100% cotton, it will be apparent that in some cases it may be desirable to use cotton blends or even a completely synthetic material. Other variations will be apparent to those of skill in the art.

Figure 8:
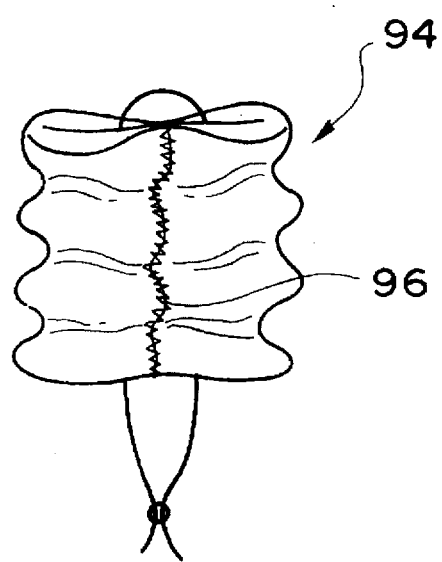
FIG. 8 is a perspective view of the tampon of FIG. 6 collapsed accordion style for insertion.

The completed tampon of FIG. 6 is then ready for use in conventional manner by insertion into the vagina. The tampon preferably is digitally inserted, for example by first folding over the fingers, or by rolling it, as illustrated in FIG. 7 at 92, or collapsing it, as illustrated in FIG. 8 at 94. If it is to be rolled, the tampon 72 is rolled lengthwise from top to bottom to form the compact package illustrated at 92, while if it is to be collapsed, the tampon 72 is simply compressed in a lengthwise direction along axis 40, as by pulling on string 84. This compression produces accordion-type folds 96 in the tampon. In either case, the user inserts the tampon digitally and adjusts its location for comfort and security, with the withdrawal string located for easy removal. The tampon may be easily removed and washed, and may be reused many times. If desired, an applicator may be used for insertion of the tampon, but that is not necessary.

Although the invention has been described in terms of a preferred embodiment, it will be apparent that numerous variations may be incorporated without departing from the true spirit and scope of the invention, as defined in the following claims.

What is claimed is:

1. A catamenial device, comprising:
    a single-piece washable, biodegradable fabric base member having a front surface, a first central axis and a second transverse axis perpendicular to said central axis;
    first and second opposed fabric-side panels folded inwardly along said transverse axis toward said central axis and overlying said front surface to produce corresponding first and second said side edges on said base member;
    first and second flaps each incorporating a corresponding one of said first and second panel side edges and being inwardly folded in transverse directions toward and overlapping said central axis;
    means securing said flaps to said base member along said central axis to form first and second elongated, multilayer, side-by-side fabric tubes on said base member; and
    a withdrawal string looped through said tubes.

2. The device of claim 1, wherein said base member is multilayer cotton cloth.

3. The device of claim 2, wherein said base member further includes a top edge and bottom edge and first and second base member side edges joined to form a peripheral edge of said base member, said base member side edges being folded transversely inwardly toward said central axis to form said first and second opposed panels.

4. The device of claim 3, further including a sewn hem at each of said upper and lower edges.

5. The device of claim 1, where said base member is a generally rectangular shape and includes opposed side edges folded transversely inwardly toward said central axis to form said opposed, overlying panels.

6. The device of claim 5, wherein said base member further includes upper and lower transverse edges longitudinally folded to produce upper and lower transverse hems.

7. The device of claim 5, wherein said means securing said flaps includes stitches securing said panel side edges to said base member.

8. The device of claim 1, wherein said base member is a multilayer, cloth material.

9. The device of claim 8, wherein said base member is a single layer cotton cloth material folded to form multiple layers.

10. A reusable, washable, internally worn feminine hygiene product, comprising:
    a single piece, folded, multilayer washable and biodegradable fabric base member having a front surface, top and bottom transverse edges, and first and second longitudinal side edges on opposite sides of a base member longitudinal central axis;

first and second flaps consisting of folded sections of said base member, said flaps incorporating said first and second side edges, respectively, parallel to said axis, said flaps extending transversely inwardly toward said axis to overlap each other and to overlie said base member front surface and said axis;

means securing said folded first and second flaps to said base member along said longitudinal axis to form corresponding first and second elongated, side-by-side, longitudinally extending multilayer fabric tubes on said base member, said tubes extending parallel to said longitudinal axis; and a cord extending through said first and second tubes.

11. The product of claim 10, wherein said base member is hemmed along said top and bottom edges.

12. The product of claim 11, wherein said fabric is moisture-absorbing.

13. The product of claim 10 wherein said securing means comprises stitching forming a seam through said flaps and said base member along said longitudinal axis.

14. The product of claim 10, wherein said cord is loosely looped through said tubes.

* * * * *